United States Patent [19]
Kojiri et al.

[11] Patent Number: 5,861,293
[45] Date of Patent: Jan. 19, 1999

[54] GENE ENCODING GLYCOSYLTRANSFERASE AND ITS USES

[75] Inventors: Katsuhisa Kojiri; Hajime Suzuki; Hisao Kondo; Hiroyuki Suda, all of Tsukuba, Japan

[73] Assignee: Banyu Pharmaceutical Co., Ltd., Tokyo, Japan

[21] Appl. No.: 750,524

[22] PCT Filed: May 31, 1995

[86] PCT No.: PCT/JP95/01065

§ 371 Date: Dec. 12, 1996

§ 102(e) Date: Dec. 12, 1996

[87] PCT Pub. No.: WO95/34663

PCT Pub. Date: Dec. 21, 1995

[30] Foreign Application Priority Data

Jun. 13, 1994 [JP] Japan .................................. 6-154127

[51] Int. Cl.⁶ .............................. C12N 9/10; C12N 15/54; C12N 15/63; C12P 21/02
[52] U.S. Cl. ............................ 435/193; 435/75; 435/119; 435/127; 435/252.3; 435/320.1; 435/325; 536/23.2
[58] Field of Search .......................... 536/23.2; 435/193, 435/320.1, 325, 252.3, 75, 119, 127

[56] References Cited

U.S. PATENT DOCUMENTS

| | | | |
|---|---|---|---|
| 4,524,145 | 6/1985 | Matson | 514/43 |
| 5,589,365 | 12/1996 | Kojiri et al. | 435/85 |
| 5,643,760 | 7/1997 | Kojiri et al. | 435/85 |

FOREIGN PATENT DOCUMENTS

| | | |
|---|---|---|
| 2111283 | 6/1994 | Canada . |
| 0269025 | 6/1988 | European Pat. Off. . |
| 0388956 | 9/1990 | European Pat. Off. . |
| 0445736 | 9/1991 | European Pat. Off. . |
| 0450327 | 10/1991 | European Pat. Off. . |
| 0528030 | 2/1993 | European Pat. Off. . |
| 0545195 | 6/1993 | European Pat. Off. . |
| 320277 | 1/1991 | Japan . |
| 9118003 | 11/1991 | WIPO . |

OTHER PUBLICATIONS

Fujiwara et al., Biochem. Biophys. Res. Comm. 187:1432–1438, 1992.

C. Herdandez, et al. "Characterization of a Streptomyces antibioticus genes cluster . . . ", Gene, vol. 134, No. 1, 1993, pp. 139–140.

M.J. Zmijewski, Jr., et al. "Biosynthesis of vanomycin: identification of TDP–glucose . . . ", FEMS Microbiology Letters, vol. 59, No. 1–2, 1989, pp. 129–134.

Katsuhisa Kojiri, et al., A New Antitumor Substance, BE–13793C, Produced By A Streptomycete, The Journal of Antibiotics, vol. 44, No. 7, Jul. 1991.

*Primary Examiner*—Eric Grimes
*Attorney, Agent, or Firm*—Sherman and Shalloway

[57] ABSTRACT

This invention relates to glycosyltransferase, genes encoding glycosyltransferase, recombinant vectors having such a gene, host cells transformed with such a recombinant vector, and uses thereof. This invention makes it possible to glycosylate indolopyrrolocarbazole derivatives conveniently and economically.

15 Claims, 1 Drawing Sheet

FIG. 1

GENE ENCODING GLYCOSYLTRANSFERASE AND ITS USES

TECHNICAL FIELD

This invention is useful in the field of medicine. More particularly, in the preparation of indolopyrrolocarbazole-derived antitumor substances, this invention is useful as a method for introducing a glycosyl group smoothly and efficiently.

BACKGROUND ART

As a result of search for antitumor substances, the present inventors found a novel antitumor substance BE-13793C (12,13-dihydro-1,11-dihydroxy-5H-indolo[2,3-a]pyrrolo[3,4-c]carbazole-5,7(6H)-dione) among microbial metabolites, and disclosed it in a previous patent application (Japanese Laid-Open Patent No. 20277/'91) [see The Journal of Antibiotics, Vol. 44, 20 pp. 723–728 (1991)]. Thereafter, they created a compound having more excellent antitumor activity by a chemical modification of BE-13793C, and disclosed it in another previous patent application (International Publication No. WO91/18003 and European Patent Laid-Open No. 0545195A1).

A problem to be solved by the present invention is to find a method which, in the preparation of indolopyrrolocarbazole derivatives having excellent antitumor activity as disclosed in the previous patent applications, can introduce a glycosyl group into such indolopyrrolocarbazole-derived antitumor substances smoothly and efficiently.

DISCLOSURE OF THE INVENTION

The present inventors have made intensive investigations with a view to solving the above-described problem, and have succeeded in cloning glycosyltransferase-encoding DNA derived from a microorganism having glycosylation capacity and expressing this gene in host cells transformed with a vector having the gene integrated thereinto. Thus, the present invention has been completed.

Accordingly, the present invention relates to genes encoding glycosyltransferase activity (including glycosyltransferase activity-encoding genes substantially biologically equivalent thereto), glycosyltransferase, recombinant vectors having a gene encoding glycosyltransferase activity (or a glycosyltransferase activity-encoding gene substantially biologically equivalent thereto), host cells transformed with such a vector, a process for preparing glycosyltransferase by culturing such a transformed host cell, and a process for preparing a glycosylated indolopyrrolocarbazole derivative by culturing such a transformed host cell.

As used herein, the term "gene encoding glycosyltransferase activity" means glycosyltransferase activity-encoding genes derived from microorganisms belonging to the order Actinomycetales or glycosyltransferase activity-encoding genes substantially biologically equivalent thereto. Among them, the glycosyltransferase activity-encoding genes derived from microorganisms belonging to the genus Saccharothrix or mutants thereof are preferred. A more preferred example thereof is that derived from Saccharothrix aerocolonigenes or a mutant thereof.

The glycosyltransferase gene derived from Saccharothrix aerocolonigenes ATCC39243 strain is a glycosyltransferase gene having the base sequence represented by the following Seq. I.D. No. 2.

Seq. I.D. No. 2

| | | | |
|---|---|---|---|
| ATGGGGGCAC | GAGTGCTGGT | GGCGACCACA | 30 |
| CCGGGGGACG | GGCACGTCAA | CCCGATGGTG | 60 |
| CCGGTCGCCC | AGGAGATGGT | CAGCCGTGGA | 90 |
| CACGAGGTGC | GGTGGTACAC | GGGAAAGGCG | 120 |
| TTCCGCTCCA | CAGTGGAACG | AACAGGAGCC | 150 |
| CGCCACGAGC | CGATGCGCGA | CGCCCACGAC | 180 |
| TTCGGCGGCA | TGCCGAGGGA | GGAGGCGTTT | 210 |
| CCCCAGCACG | CGGGGCTGAC | CGGGATCACG | 240 |
| GGGATGATCG | CGGGGTTCAG | GGACATCTTC | 270 |
| ATCGAACCCG | CGGCCGACCA | GATGACAGAC | 300 |
| CTGCTGGCAC | TGCTGGAGGA | CTTCCCGGCC | 330 |
| GACGTGCTCG | TGACCGACGA | GACCTTCTTC | 360 |
| GGCGCGGGTT | TCGTCAGTGA | GCGCACGGGA | 390 |
| ATCCCCGTCG | CCTGGATCGC | CACGTCGATC | 420 |
| TACGTCTTCA | GCAGCCGCGA | CACGGCACCG | 450 |
| CTCGGGCTGG | GCCTGCCGCC | CAGCAGCTCC | 480 |
| AGGCTGGGCA | GGCTGCGCAA | CACCGTGCTC | 510 |
| AAACAGCTGA | CAGACCGTGT | CGTCATGCGA | 540 |
| GATCTCCGGC | GGCACGCGGA | CGTGGTGCGC | 570 |
| GACCGCGTCG | GCCTGCCCCG | CATCCGCAAG | 600 |
| GGGGCGTTCG | AGAACATCAT | GCGCACGCCC | 630 |
| GACCTCTACC | TGCTGGGCAC | CGTGCCGTCC | 660 |
| TTCGAGTACC | CGCGAGGCGA | CATGCCACCC | 690 |
| GAGGTGAGGT | TCGTCGGCCC | GTTCGTGAGC | 720 |
| CCTGCTCCGC | CGGACTTCAC | CCCACCGGCG | 750 |
| TGGTGGGGCG | AGCTCGACTC | CGGCCGGCCC | 780 |
| GTCGTCCACG | TCACCCAGGG | CACCGTCGCC | 810 |
| AACGACGCGG | AACGCCTGCT | GCTCCCCGCC | 840 |

-continued
Seq. I.D. No. 2

```
ATCCGAGCGC TGGCAGCCGA AGACGTGCTC  870
GTGGTCGCGA CCACCGGTGC CCCTCTGGAA  900
CTGGAGCCGA TGCCGGCCAA CGTGCGGGTG  930
GAACGGTTCA TCCCGCATCA CGCATTGCTT  960
CCCCACGTGG ACGCCATGGT GACCAACGGG  990
GGATACGGCG GCGTCAACAC GGCGCTCGCA 1020
CACGGCGTGC CGCTGGTCGT CGCGCGCACC 1050
GAGGAGAAGC ACGAGGTCGC GGCCAGAGTG 1080
AGCTGGTCAG GTGCGGGTGT TCACCTGAAG 1110
AAGCGCAGGC TGTCCGAACG GGACATCAGA 1140
CGGGCCGTGC GCGCCGTTCT CGACGAGCCG 1170
CGCTTCCGGG TCCACGCGGC GCGGCTGCGG 1200
GACGAGTACG CGGCGCGCGA CGCGGTCGTG 1230
GACGCGTCGA CCTGA                 1245
```

The amino acid sequence of the transferase encoded by the glycosyltransferase gene represented by Seq. I.D. No. 2 is an amino acid sequence represented by the following Seq. I.D. No. 1.

Seq. I.D. No. 1

```
Met Gly Ala Arg Val Leu Val Ala Thr Thr Pro Gly
1               5                   10
Asp Gly His Val Asn Pro Met Val Pro Val Ala Gln
            15              20
Glu Met Val Ser Arg Gly His Glu Val Arg Trp Tyr
25              30                      35
Thr Gly Lys Ala Phe Arg Ser Thr Val Glu Arg Thr
            40                  45
Gly Ala Arg His Glu Pro Met Arg Asp Ala His Asp
50                  55                      60
Phe Gly Gly Met Pro Arg Glu Glu Ala Phe Pro Gln
                65              70
His Ala Gly Leu Thr Gly Ile Thr Gly Met Ile Ala
            75                  80
Gly Phe Arg Asp Ile Phe Ile Glu Pro Ala Ala Asp
85                  90                      95
Gln Met Thr Asp Leu Leu Ala Leu Leu Glu Asp Phe
                100             105
Pro Ala Asp Val Leu Val Thr Asp Glu Thr Phe Phe
            110             115                 120
```

-continued
Seq. I.D. No. 1

```
Gly Ala Gly Phe Val Ser Glu Arg Thr Gly Ile Pro
                125                 130
Val Ala Trp Ile Ala Thr Ser Ile Tyr Val Phe Ser
            135                 140
Ser Arg Asp Thr Ala Pro Leu Gly Leu Gly Leu Pro
145                 150                 155
Pro Ser Ser Ser Arg Leu Gly Arg Leu Arg Asn Thr
                160                 165
Val Leu Lys Gln Leu Thr Asp Arg Val Val Met Arg
            170                 175             180
Asp Leu Arg Arg His Ala Asp Val Val Arg Asp Arg
                185                     190
Val Gly Leu Pro Arg Ile Arg Lys Gly Ala Phe Glu
            195                 200
Asn Ile Met Arg Thr Pro Asp Leu Tyr Leu Leu Gly
205                 210                 215
Thr Val Pro Ser Phe Glu Tyr Pro Arg Gly Asp Met
                220                 225
Pro Pro Glu Val Arg Phe Val Gly Pro Phe Val Ser
        230                 235                 240
Pro Ala Pro Pro Asp Phe Thr Pro Pro Ala Trp Trp
                245                 250
Gly Glu Leu Asp Ser Gly Arg Pro Val Val His Val
            255                 260
Thr Gln Gly Thr Val Ala Asn Asp Ala Glu Arg Leu
265                 270                 275
Leu Leu Pro Ala Ile Arg Ala Leu Ala Ala Glu Asp
                280                 285
Val Leu Val Val Ala Thr Thr Gly Ala Pro Leu Glu
            290                 295             300
Leu Glu Pro Met Pro Ala Asn Val Arg Val Glu Arg
                305                 310
Phe Ile Pro His His Ala Leu Leu Pro His Val Asp
                315                 320
Ala Met Val Thr Asn Gly Gly Tyr Gly Gly Val Asn
325                 330                 335
Thr Ala Leu Ala His Gly Val Pro Leu Val Val Ala
            340                 345
Arg Thr Glu Glu Lys His Glu Val Ala Ala Arg Val
            350                 355             360
Ser Trp Ser Gly Ala Gly Val His Leu Lys Lys Arg
                365                 370
Arg Leu Ser Glu Arg Asp Ile Arg Arg Ala Val Arg
            375                 380
Ala Val Leu Asp Glu Pro Arg Phe Arg Val His Ala
385                 390                 395
Ala Arg Leu Arg Asp Glu Tyr Ala Ala Arg Asp Ala
                400                 405
Val Val Asp Ala Ser Thr
            410
```

The term "glycosyltransferase activity" means the ability to glycosylate, for example, an indolopyrrolocarbazole derivative of the general formula wherein R, $X^1$ and $X^2$ represent hydrogen atoms or substituent groups, and thereby convert it to a compound of the general formula wherein R, $X^1$ and $X^2$ have the same meanings as described above.

Specific examples of the aforesaid indolopyrrolocarbazole derivative include indolopyrrolocarbazole derivative in which each of $X^1$ and $X^2$ is a hydrogen atom, a halogen atom, an amino group, a mono(lower alkyl)amino group, a di(lower alkyl)amino group, a hydroxyl group, a lower alkoxy group, an aralkoxy group, a carboxyl group, a lower alkoxycarbonyl group, a lower alkanoyloxy group or a lower alkyl group, and R is a hydrogen atom, an amino group, a formylamino group, a lower alkanoylamino group, a mono (lower alkyl)amino group, a di(lower alkyl)amino group, a hydroxyl group, a lower alkoxy group, an aralkoxy group, an aralkyl group or a lower alkyl group. Preferred examples thereof include indolopyrrolocarbazole derivative in which each of $X^1$ and $X^2$ is a hydroxyl group and R is a hydrogen atom, a lower alkyl group or an amino group.

The indolopyrrolocarbazole derivatives which are used as starting compounds in the present invention can be prepared according to any well-known process such as the double Fischer indolization process [see Journal of Organic Chemistry, Vol. 54, pp. 824–828 (1989)]. Another usable process is the process for the synthesis of indolocarbazoles which is described in Journal of the Chemical Society, Perkin Transactions I, pp. 2475–2480 (1990). Moreover, the synthesis processes described in Tetrahedron, Vol. 44, pp. 2887–2892 (1988) and Japanese Patent Laid-Open No. 20277/'91 can also be employed. Specific procedures for the preparation of starting compounds are described in Reference Examples 1 and 2.

Now, the methods for the cloning of a gene encoding glycosyltransferase and for the determination of its base sequence, the process for preparing a compound of the general formula [II] by culturing a transformed host cell in the presence of an indolopyrrolocarbazole derivative of the general formula [I], and the process for preparing the compound of the general formula [III] by transforming *Streptomyces mobaraensis*, which is a bacterium capable of producing BE-13793C, with the aforesaid gene and culturing the resulting transformed strain are more specifically described hereinbelow.

(1) Process for the preparation of DNA encoding glycosyltransferase

DNA is isolated from a microorganism capable of introducing a glycosyl group into indolopyrrolocarbazole derivatives, such as *Saccharothrix aerocolonigenes* ATCC39243 strain, cleaved into appropriate DNA fragments, and integrated into suitable plasmid vectors. After the resulting recombinant plasmids are used to transform hosts, the resulting transformants are cultured. Then, transformants having the ability to convert an indolopyrrolocarbazole derivative (e.g., BE-13793C) to 12,13-dihydro-1,11-dihydroxy-13-(β-D-glucopyranosyl)-5H-indolo[2,3-a]pyrrolo[3,4-c]carbazole-5,7(6H)-dione (hereinafter referred to as ED-110) are screened to obtain transformants containing the desired DNA. The desired DNA can be obtained by isolating plasmids from the aforesaid transformants and cutting out the cloned DNA from these plasmids.

More specifically, the glycosyltransferase DNA can be prepared in the following manner. DNA is isolated from a microorganism (e.g., *Saccharothrix aerocolonigenes* ATCC39243 strain) having the ability to introduce a glycosyl group into indolopyrrolocarbazole derivatives, according to a per se known method. The resulting DNA is fragmented with a suitable restriction enzyme and integrated into a plasmid vector derived from *Escherichia coli* or actinomycetes to construct a library. As the plasmid into which the DNA is introduced, there may be used any plasmid that can be replicated and retained in a host. Plasmids derived from *Escherichia coli*, actinomycetes and the like are preferred, and plasmids derived from actinomycetes are more preferred. Specific examples of plasmid vectors derived from *Escherichia coli* include pBR322 [Gene, Vol. 2, p. 95 (1977)], pUC118 [Method in Enzymology, Vol. 153, p. 3 (1987)] and pUC119 [Method in Enzymology, Vol. 153, p. 3 (1987)], and specific examples of plasmid vectors derived from actinomycetes include pIJ702 [Journal of General Microbiology, Vol. 129, p. 2703 (1983)], pIJ922 [Gene, Vol. 35, p. 223 (1985)], pVE28 [PLASMID, Vol. 16, p. 187 (1986)] and pSK21-1 [The Journal of Antibiotics, Vol. 37, No. 9, p. 1026 (1984)]. In order to integrate the desired DNA into a plasmid vector, there may be employed any of per se known methods including, for example, the method of T. Maniatis et al. (Molecular Cloning, Cold Spring Harbor Laboratory, p. 239, 1982) and the method of D. A. Hopwood et al. [Genetic Manipulation of Streptomyces—a Laboratory Manual (1985)].

Next, the plasmid vector thus obtained is introduced into a host. Useful hosts include, for example, *Escherichia coli* and actinomycetes. Specific examples of *Escherichia coli* include *Escherichia coli* MV1184 [Method in Enzymology, Vol. 153, p. 3 (1987)], HB101 [Journal of Molecular Biology, Vol. 41, p. 459 (1969)] and JM109 [Gene, Vol. 33, p. 103 (1985)]. Specific examples of actinomycetes include *Streptomyces lividans* TK21 and its derivatives, *Streptomyces coelicolor*, *Streptomyces pavulus* [Genetic Manipulation of Streptomyces—a Laboratory Manual, pp. 257–267 (1985)], *Streptomyces kasugaensis* [The Journal of Antibiotics, Vol. 37, No. 9, p. 1026 (1984)] and *Streptomyces mobaraensis* BA13793 [The Journal of Antibiotics, Vol. 44, p. 723 (1991)]. (*Streptomyces mobaraensis* BA13793 strain was deposited on Jan. 20, 1989 with the Research Institute of Microbiological Technology, the Agency of Industrial Science and Technology, the Ministry of International Trade and Industry, and its accession number is FERM P-10489. Then, this strain was transferred on Mar. 1, 1990 to international deposition based on the Budapest Treaty, and its accession number is FERM BP-2785.) Among them, *Streptomyces lividans* TK21, *Streptomyces mobaraensis* BA13793 and *Escherichia coli* MV1184 are preferred.

In order to transform a host with the plasmid, there may be used any of per se known methods. For example, when *Escherichia coli* is used, the calcium chloride method of T. Maniatis et al. [Molecular Cloning, Cold Spring Harbor Laboratory, p. 239 (1982)], the calcium chloride/rubidium chloride method or the like may be employed. For example, when an actinomycete is used, the protoplast method of D. A. Hopwood et al. [Genetic Manipulation of Streptomyces—a Laboratory Manual (1985)] or the like may be employed. In order to select a strain having the desired DNA, the *Escherichia coli* or the actinomycete transformants obtained in the above-described manner may be screened by growing each transformant in a liquid medium, adding an indolopyrrolocarbazole derivative (e.g., BE-13793C) to the culture medium, and detecting ED-110 having a glycosyl group introduced thereinto. Specifically, a strain capable of producing ED-110 can be selected by extracting the BE-13793C-containing culture medium with methyl ethyl ketone, evaporating the extract to dryness, dissolving the residue in tetrahydrofuran, and subjecting it to silica gel thin-layer chromatography using chloroform/methanol/tetrahydrofuran (3:1:1) as the developing solvent. The resulting cloned glycosyltransferase DNA may further be subcloned into a plasmid (e.g., pBR322, pUC18, pUC19, pUC118, pUC119 or pIJ702) as required. The base sequence of the DNA thus obtained can be determined according to any of per se known methods including, for example, the dideoxy method [J. Messing et al., Nucleic Acids Research, Vol. 9, p. 309 (1981)] and the deaza method [S. Mizusawa et al., Nucleic Acids Research, Vol. 14, p. 1319 (1986)].

(2) Method for glycosylating an indolopyrrolocarbazole derivative by culturing a transformed host cell in the presence of the derivative The introduction of a glycosyl group into an indolopyrrolocarbazole derivative may be carried out by culturing *Escherichia coli* or an actinomycete which has been transformed with a plasmid vector having integrated thereinto a DNA fragment containing a glycosyltransferase-encoding gene, according to a per se known method, and adding the indolopyrrolocarbazole derivative to the culture medium. Preferably, the microorganism used for this purpose is, for example, a transformant obtained by using an actinomycete as the host. More preferably, it is, for example, a transformant obtained by using *Streptomyces lividans* TK21 or the like as the host. Moreover, in the direct fermentative preparation of ED-110, it is preferable to use, for example, a transformant obtained by using *Streptomyces mobaraensis* BA13793 strain capable of producing BE-13793C or a mutagenically treated strain thereof as the host. Thus, a glycosylated indolopyrrolocarbazole can be prepared by culturing the above-described transformant according to a per se known method. The microorganism is cultured in a liquid medium which contains carbon sources such as glucose, glycerin, dextrin, sucrose, starch and molasses, and nitrogen sources such as corn gluten meal, cotton seed meal, soybean meal, peptone, yeast extract, meat extract and inorganic nitrogen compounds (e.g., various ammonium salts and nitrates) and which further contains various inorganic salt compounds capable of releasing phosphate, magnesium, sodium, potassium, chloride and/or sulfate ions, trace elements necessary for growth, various antifoaming agents and the like as required. This liquid culture can be carried out according to any of various culture techniques such as standing culture, spinner culture, shaking culture and aerated culture. In particular, shaking culture and deep-aerated spinner culture are preferred. When a transformant obtained by using *Streptomyces lividans* TK21 as the host, the incubation temperature is suitably in the range of 20° to 37° C. and preferably 25° to 30° C. The pH of the culture medium is preferably in the range of 4 to 8. The incubation time may range from 2 to 20 days, preferably from 7 to 15 days, starting from the addition of the indolopyrrolocarbazole derivative. When a glycosylated indolopyrrolocarbazole derivative is directly prepared by culturing a transformant obtained by using *Streptomyces mobaraensis* BA13793 strain as the host, its culture may be carried out in the same manner as described above, except that no indolopyrrolocarbazole derivative is added.

In order to recover the indolopyrrolocarbazole derivative having a glycosyl group introduced thereinto from the resulting culture, any separation means that is commonly used to recover a metabolite produced by a microorganism from a culture thereof may be suitably used. Since the desired compound is present in the culture supernatant and the bacterial cells, it can be purified from the culture supernatant or the bacterial cells by using any of common separation means (e.g., solvent extraction, ion-exchange resin treatment, adsorption or partition chromatography, and gel filtration) or a combination thereof. Moreover, high-performance liquid chromatography, thin-layer chromatography and the like may also be used for the purpose of extraction and purification.

The present invention is more specifically explained with reference to the following examples and reference examples. However, it is to be understood that the present invention is not limited thereto.

Example 1

(1)

Preparation of chromosomal DNA from a strain of *Saccharothrix aerocolonigenes* and its cleavage with restriction enzymes

*Saccharothrix aerocolonigenes* ATCC39243 strain which had been grown by slant culture on a starch-inorganic salt agar medium (ISP4; manufactured by Difco) was inoculated into a 500 ml Erlenmeyer flask containing 110 ml of Tryptocase Soy Broth (hereinafter abbreviated as TSB) medium (manufactured by Becton Dickinson Co.), and incubated at 28° C. on a rotary shaker (180 revolutions per minute) for 3 days. Then, 2 ml of this culture medium was inoculated into TSB medium having 0.8% glycine added thereto, and incubated in the same manner for 2 days. 20 ml of the aforesaid culture medium was centrifuged to collect bacterial cells. These bacterial cells were centrifugally washed twice with TEG buffer [50 mM Tris-HCl buffer (pH 8.0), 10 mM EDTA·2Na, 50 mM glucose]. After the washed bacterial cells were resuspended in 10 ml of TEG buffer, 5 ml of a solution of lysozyme (manufactured by Sigma Co.; dissolved in TEG buffer at a concentration of 12 mg/ml) was added thereto and the resulting mixture was reacted at 37° C. for 1 hour. After 2 ml of 10% sodium dodecyl sulfate was added to lyse the bacterial cells, the mixture was alternately treated with phenol/chloroform (1:1) saturated with TE buffer [10 mM Tris-HCl pH 8.0), 1 mM EDTA-2Na], and chloroform/isoamyl alcohol (24:1). The aqueous layer was separated, 1/10 volume of 1 mg/ml ribonuclease A (RNase A; manufactured by Sigma Co.) was added thereto, and the resulting solution was incubated at 37° C. for 1 hour. After this solution was treated with an equal volume of chloroform/isoamyl alcohol (24:1), the aqueous layer was transferred to an autoclaved beaker and 1/10 volume of 3.3M sodium acetate was added thereto. While two volumes of cold ethanol was being added thereto, the solution was stirred with a glass rod to collect DNA thereon. The collected DNA was washed with 75% ethanol, dried and then dissolved in 9 ml of 0.1-fold SSC buffer [0.15M sodium chloride, 0.015M sodium citrate (pH 7.0)]. To the resulting DNA solution was added 1/10 volume of 3.3M sodium acetate. While 0.54 volume of isopropanol was being added thereto, the solution was stirred with a glass rod to collect DNA thereon. The collected DNA was washed with 75% ethanol, dried and then dissolved in an appropriate amount of TE buffer.

Next, 20 units of the restriction enzyme Sau3AI (manufactured by Takara Shuzo Co., Ltd.) was added to 50 μg of the above chromosomal DNA, and they were reacted in H buffer [50 mM Tris-HCl (pH 7.5), 10 mM magnesium chloride, 1 mM dithiothreitol, 100 mM sodium chloride] at 37° C. for 1 minute. All of the restriction enzymes used hereafter were ones manufactured by Takara Shuzo Co., Ltd. After completion of the reaction, the restriction enzyme was inactivated by treatment with phenol and extraction with ether. Then, the resulting DNA fragments were subjected to electrophoresis in 1.0% agarose/100 mM Tris-boric acid/2 mM EDTA·2Na (pH 8.3), and a DNA fraction having a size of about 2–10 Kbp was extracted with GENECLEAN II (manufactured by BIO 101 Co.).

(2)

Insertion of chromosomal DNA fragments into plasmid vector DNA

Streptomyces lividans TK21 strain, which is an actinomycete having the actinomycetal plasmid vector pIJ702, was inoculated into four 500 ml Erlenmeyer flasks containing 110 ml of the aforesaid TSB medium having 25 μg/ml of thiostrepton added thereto, and incubated at 28° C. on a rotary shaker (180 revolutions per minute) for 3 days. Bacterial cells were collected from 440 ml of this culture medium and centrifugally washed with the aforesaid TEG buffer. 50 ml of TEG buffer containing 2 mg/ml of lysozyme was added to the washed bacterial cells, and this suspension was allowed to stand at 37° C. for 30 minutes. After the addition of 50 ml of 0.2N NaOH/1% sodium dodecyl sulfate (SDS), the resulting mixture was allowed to stand at 0° C. for 5 minutes. Then, after the addition of 50 ml of 2.55M potassium acetate (pH 4.8), the resulting mixture was allowed to stand at 0° C. for 10 minutes and centrifuged. After the supernatant was treated with phenol, 3/5 volume of a polyethylene glycol 6000 (PEG-6000)/2.5M sodium chloride solution was added to the aqueous layer, and the resulting mixture was allowed to stand at 0° C. for 1 hour and centrifuged to precipitate DNA. This precipitate was dissolved in 4 ml of the aforesaid TE buffer and subjected to ethidium bromide-cesium chloride equilibrium density gradient centrifugation to obtain plasmid DNA. The pIJ702 plasmid thus obtained was digested with the restriction enzyme BglII and incubated with 2 units of bacterial alkaline phosphatase (manufactured by Takara Shuzo Co. , Ltd.) at 65° C. for 30 minutes. Then, the alkaline phosphatase was removed by treatment with phenol and extraction with ether. 1.0 μg of the phosphatase-treated plasmid DNA was mixed with 5 μg of the chromosomal DNA fragments obtained in (1), and they were ligated by means of a DNA ligation kit (manufactured by Takara Shuzo Co., Ltd.).

(3)

Transformation of Streptomyces lividans TK21 strain

The Transformation of Streptomyces lividans TK21 strain was carried out according to a modification of the method of D. A. Hopwood et al. (Genetic Manipulation of Streptomyces—a Laboratory Manual). Specifically, Streptomyces lividans TK21 strain which had been grown by slant culture on a yeast-malt agar medium (ISP2; manufactured by Difco) was inoculated into a 500 ml Erlenmeyer flask containing 110 ml of the aforesaid TSB medium, and incubated at 28° C. on a rotary shaker (180 revolutions per minute) for 3 days. Then, 2 ml of this culture medium was inoculated into TSB medium having 0.5% glycine added thereto, and incubated in the same manner for 20 hours. Bacterial cells were collected from 40 ml of this culture medium and centrifugally washed twice with 0.35M P3 medium [11.98% sucrose, 0.4% sodium chloride, 0.1% magnesium chloride hexahydrate, 0.074% calcium chloride dihydrate, 0.573% N-tris(hydroxymethyl)methylaminoethane-sulfonic acid buffer (TES; manufactured by Dotite Co.; pH 7.2)]. Then, 20 ml of 0.35M PWP medium [11.98% sucrose, 0.4% sodium chloride, 0.2% magnesium chloride hexahydrate, 0.294% calcium chloride dihydrate, 0.573% TES buffer (pH 7.2)] was added to the washed bacterial cells, followed by intimate mixing. Thereafter, lysozyme was added thereto so as to give a final concentration of 10 mg/ml. This suspension was incubated at 30° C. for 60 minutes, passed through sterilized absorbent cotton to remove hyphae, and centrifuged. The precipitate was centrifugally washed twice with 0.35M PWP medium and suspended in 0.35M PWP medium so as to give a density of $10^9$ to $10^{10}$ protoplasts/ml . After a solution of the plasmid vector having DNA ligated thereinto was added to 100 μl of the protoplast suspension, 0.5 ml of 0.35M PWP medium having 30% PEG-2000 dissolved therein was further added thereto and mixed therewith. After 1 minute, 5 ml of 0.35M PWP medium was added thereto and protoplasts were collected by centrifugation. Then, these protoplasts were suspended in an appropriate amount of 0.35M PWP medium. 100 μl each of this suspension was applied onto 0.35M R3 agar plates [11.98% sucrose, 0.81% magnesium chloride hexahydrate, 0.05% potassium chloride, 0.22% calcium chloride dihydrate, 0.02% potassium dihydrogen phosphate, 1% glucose, 0.4% polypeptone, 0.04% yeast extract (manufactured by Difco), 0.573% TES buffer (pH 7.2), 2.2% agar], and incubated at 28° C. overnight. Then, 2.5 ml each of a melanin-producing soft agar medium (0.2% glucose, 1.0% yeast extract, 0.05% L-tyrosine, 0.5% sodium chloride, 0.4% agar) containing 250 μg/ml of thiostrepton was layered over these 0.35M R3 agar plates. Thereafter, the incubation was continued at 28° C. for an additional one week.

(4)

Detection of the desired gene

About 5,000 thiostrepton-resistant, non-melanin-productive strains obtained in the manner described in (3)

were examined for glycosyltransferase activity. The activity was measured in terms of the activity for converting BE-13973C used as the substrate to ED-110. Specifically, each transformed strain was inoculated into a test tube containing 5 ml of a glycosylating medium [0.5% glucose, 8.0% dextrin, 0.25% L-threonine, 0.3% yeast extract, 0.1% magnesium sulfate heptahydrate, 0.2% calcium carbonate, 0.05% calcium chloride, 0.0002% ferrous sulfate, 0.00004% cupric chloride, 0.00004% manganese chloride, 0.00004% cobalt chloride, 0.00008% zinc sulfate, 0.00008% sodium borate, 0.00024% ammonium molybdate (pH 7.2)] to which thiostrepton had been added so as to give a final concentration of 20 µg/ml, and incubated at 28° C. on a rotary shaker (300 revolutions per minute) for 3 days. Thereafter, BE-13793C dissolved in methanol/tetra-hydrofuran (2:1) was added thereto so as to give a final concentration of 40 µg/ml, and the incubation was continued at 28° C. in the same manner for 2 days. The resulting culture medium was extracted with 5 ml of methyl ethyl ketone. After the methyl ethyl ketone layer was concentrated to dryness under reduced pressure, the resulting residue was dissolved in a small amount of tetrahydrofuran and subjected to thin-layer chromatography (TLC). Silica gel (Kieselgel 60; manufactured by Merck) was used on the thin-layer plate, and chloroform/methanol/tetrahydrofuran (3:1:1) was used as the developing solvent. In this case, the Rf value is 0.73 for BE-13793C and 0.36 for ED-110, so that they can be distinguished on the thin layer. When about 5,000 transformed strains were examined in this manner, one of them was found to have glycosyltransferase activity. Since this transformed strain has the plasmid pNGT206 as will be described later, it is conveniently designated as *Streptomyces lividans* TK21 (pNGT206). The plasmid pNGT206 contains a gene encoding glycosyltransferase.

(5)
Separation and analysis of the recombinant plasmid

Figure 1:
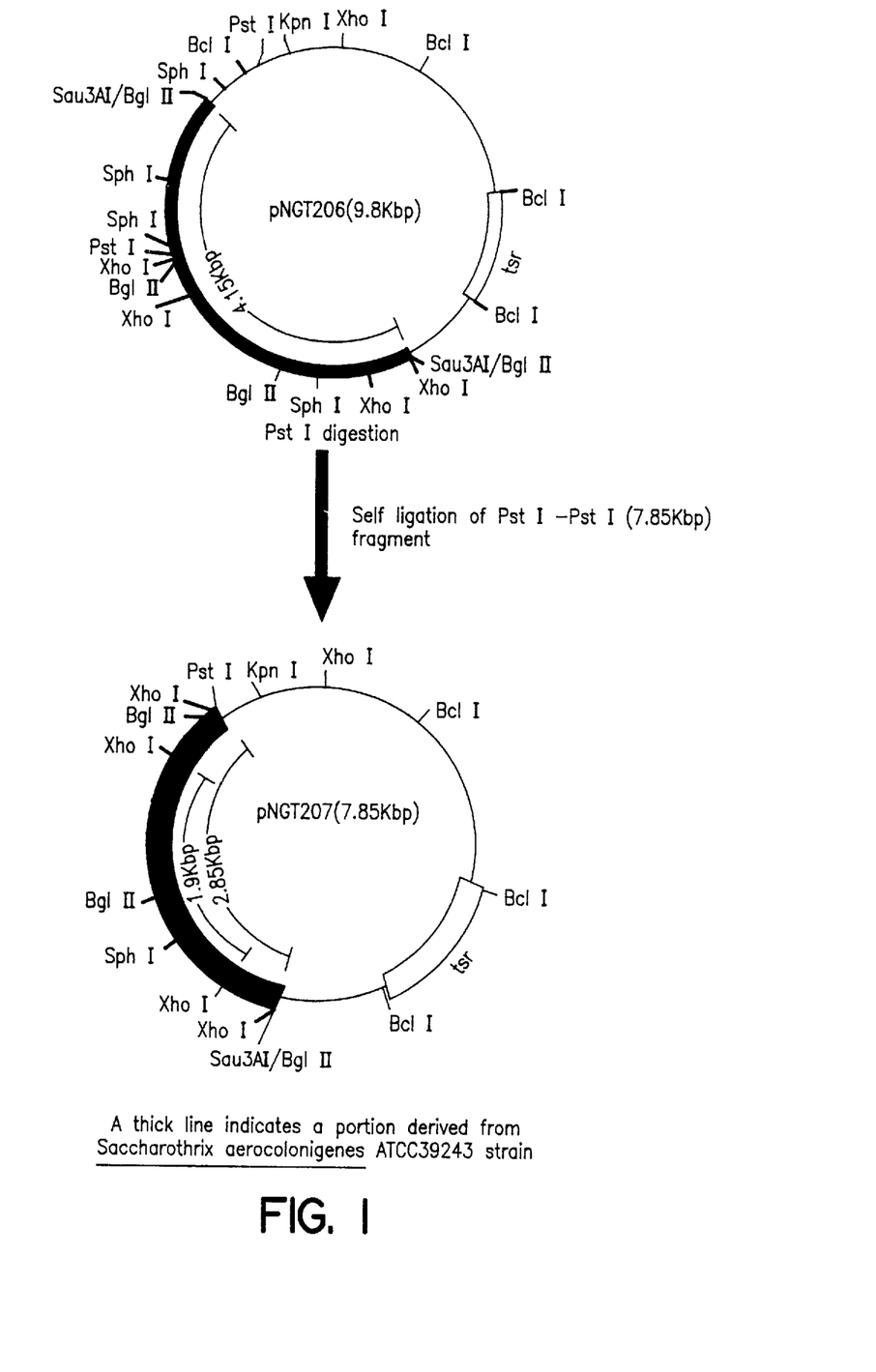
FIG. 1 is a map showing the restriction enzyme cleavage sites of the plasmids pNGT206 and pNGT207 containing a gene encoding glycosyltransferase in accordance with the present invention and wherein the thick line indicates a portion derived from *Saccharothrix aerocolonigenes* ATCC 39243 strain.

According to the procedure described in (2), the DNA of the plasmid pNGT206 was purified from *Streptomyces lividans* TK21 (pNGT206) strain obtained in (4). The resulting plasmid was cleaved with various restriction enzymes to construct a restriction enzyme cleavage map. The results thus obtained are shown in FIG. 1. The length of the inserted DNA fragment was 4.15 Kbp.

(6)
Preparation of pNGT207 from pNGT206

The plasmid pNGT206 obtained in (5) was reacted with the restriction enzyme PstI and subjected to electrophoresis in 1.0% agarose. Then, a 7.95 Kbp DNA fragment was extracted with GENECLEAN II. Using a DNA ligation kit, the extracted DNA fragment was ligated into the plasmid vector pIJ702. Then, according to the procedure described in (3), *Streptomyces lividans* TK21 strain was transformed with this vector to obtain a thiostrepton-resistant transformed strain. According to the procedure described in (4), it was confirmed that this transformed strain had glycosyltransferase activity. The strain obtained in the above-described manner was named *Streptomyces lividans* TK21 (pNGT207) strain and deposited with the Research Institute of Biotechnology and Industrial Technology, the Agency of Industrial Science and Technology (under the accession number of FERM P-14365). This strain was transferred on May 9, 1995 to international deposition based on the Budapest Treaty, and its accession number is FERM BP-5091. The restriction enzyme cleavage map of the plasmid pNGT207 is shown in FIG. 1. The length of the inserted DNA fragment was 2.85 Kbp.

(7)
Preparation of a subcloned plasmid from the plasmid pNGT207 and determination of its base sequence First of all, the plasmid pNGT207 was reacted with the restriction enzyme XhoI and subjected to electrophoresis in agarose. Then, a 1.9 Kbp DNA fragment was extracted with GENECLEAN II. Using a DNA ligation kit, the extracted DNA fragment was mixed with and ligated into the *Escherichia coli* plasmid vector pUC119 (manufactured by Takara Shuzo Co., Ltd.) which had been digested with SalI. After ligation, *Escherichia coli* MV1184 strain was transformed with this recombinant plasmid. The transformation of *Escherichia coli* MV1184 strain was carried out according to the following procedure. First of all, *Escherichia coli* MV1184 strain was inoculated into 100 ml of SOB medium [2% trypton (manufactured by Difco), 0.5% yeast extract, 10 mM sodium chloride, 2.5 mM potassium chloride, 10 mM magnesium chloride, 10 mM magnesium sulfate), and incubated with shaking at 37° C. overnight. Then, 0.6 ml of this culture medium was inoculated into the same SOB medium and incubated at 37° C. As soon as the culture medium reached an absorbance of 11 at 550 nm, 50 ml of the culture medium was centrifuged to collect bacterial cells. These bacterial cells were suspended in 16 ml of TFB solution (10 mM 2-(N-morpholino)ethanesulfonic acid buffer (pH 6.3), 100 mM potassium chloride, 45 mM manganese chloride, 10 mM calcium chloride, 3 mM cobalt chloride] and allowed to stand at 0° C. for 10 minutes. Thereafter, the bacterial cells were collected by centrifugation and resuspended in 3.8 ml of TFB solution. After the addition of 133 µl of dimethyl sulfoxide, the suspension was allowed to stand at 0° C. for 15 munites. Thereafter, 133 µl of dimethyl sulfoxide was added thereto and the suspension was allowed to stand at 0° C. for 5 munites. The mixture having undergone the above-described DNA ligation was added to 100 µl of this suspension, and the resulting mixture was allowed to stand at 0° C. for 1 hour. After this mixture was heat-treated at 42° C. for 45 seconds, 400 µl of SOB medium was added thereto and the resulting mixture was incubated with shaking at 37° C. for 1 hour. Thereafter, 100 µl each of the mixture was applied to X-Gal plates (1.0% trypton, 0.25% sodium chloride, 1.5% agar) containing ampicillin (100 µg/ml), 5-bromo-4-chloro-3-indolyl-β-D-gal actoside (X-gal; 40 µg/ml) and isopropyl-β-D-thiogalactopyranoside (23.8 µg/ml), and incubated statically at 37° C. overnight. Then, a transformed strain of *Escherichia coli* forming an ampicillin-resistant white colony was selected, and the plasmid were extracted and purified from this transformed strain. The purification of the recombinant plasmid was carried out according to the procedure described in (2). However, when the plasmid DNA of *Escherichia coli* was to be purified, the transformed strain was inoculated into a 500 ml Erlenmeyer flask containing 110 ml of twofold YT medium [0.8% bactotrypton, 0.5% yeast extract, 0.5% sodium chloride (pH 7.6)] containing 100 µg/ml of ampicillin, and incubated at 37° C. on a rotary shaker (200 revolutions per minute) overnight.

The 0.9 Kbp XhoI fragment of pNGT207 shown in FIG. 1 encodes a protein having glycosyltransferase activity. Using the *Escherichia coli* plasmid vectors pUC118 (manufactured by Takara Shuzo Co., Ltd.) and pUC119, its base sequence was determined by means of a base sequence determination kit (BcaBEST™ Dideoxy Sequencing Kit; manufactured by Takara Shuzo Co., Ltd.).

(8)
Analysis of the structure of the glycosyltransferase gene

The base sequence data thus obtained were analyzed by means of the DNA analysis program GCG (a program made by Genetic Computer Group Co.). The base sequence so determined consists of 1,898 base pairs, has an open reading frame of 1,245 base pairs extending from the 285th base (ATG) to the 1529th base (TGA), and encodes a protein composed of 414 amino acid residues.

(9)
Transformation of *Streptomyces mobaraensis* BA13793 strain with the plasmid pNGT207

*Streptomyces mobaraensis* BA13793 strain which had been grown by slant culture on ISP4 medium containing 25 $\mu$g/ml of thiostrepton was inoculated into a 500 ml Erlenmeyer flask containing 110 ml of TSB medium, and incubated at 28° C. on a rotary shaker (180 revolutions per minute) for 3 days. Moreover, 2 ml of this culture medium was inoculated into TSB medium having 0.8% glycine added thereto, and incubated under the same conditions as described above for 2 days. 40 ml of this culture medium was centrifuged to collect bacterial cells, which were centrifugally washed twice with sterilized 0.5M P3 medium [17.1% sucrose, 0.4% sodium chloride, 0.1% magnesium chloride hexahydrate, 0.074% calcium chloride di hydrate, 0.573% TES buffer (pH 7.2)]. Then, 20 ml of sterilized 0.5M PWP medium [17.1% sucrose, 0.4% sodium chloride, 0.2% magnesium chloride hexahydrate, 0.294% calcium chloride dihydrate, 0.573% TES buffer (pH 7.2)] was added to the washed bacterial cells, followed by intimate mixing. Thereafter, lysozyme was added thereto so as to give a final concentration of 750 $\mu$g/ml, and Achromopeptidase (manufactured by Wako Pure Chemical Industries Ltd.) was added thereto so as to give a final concentration of 500 $\mu$g/ml. This suspension was incubated at 37° C. for 1 hour, passed through sterilized absorbent cotton to remove hyphae, and centrifuged. The precipitate was centrifugally washed twice with 0.5M PWP medium and suspended in 0.5M PWP medium so as to give a density of $10^9$ to $10^{10}$ protoplasts/ml. After an appropriate amount of the plasmid pNGT207 was added to 100 $\mu$l of the protoplast suspension, 0.5 ml of 0.5M PWP medium having 30% PEG-2000 dissolved therein was further added thereto and mixed therewith. After 1 minute, 5 ml of 0.5M PWP medium was added thereto and the protoplasts were centrifugally washed. Then, these protoplasts were suspended in an appropriate amount of 0.5M PWP medium. 100 $\mu$l each of this suspension was applied onto 0.5M R3 agar plates [17.1% sucrose, 0.81% magnesium chloride hexahydrate, 0.05% potassium chloride, 0.22% calcium chloride dihydrate, 0.02% potassium dihydrogen phosphate, 1% glucose, 0.4% polypeptone, 0.04% yeast extract, 0.573% TES buffer (pH 7.2), 1.0% gellan gum], and incubated at 37° C. Then, 2.5 ml each of a melanin-producing soft agar medium [comprising 0.5M R3 agar medium in which the gellan gum is replaced by 0.4% low-melting agarose (manufactured by Nakarai Co., Ltd.)] was layered over these agar plates. Thereafter, the incubation was continued at 28° C. for an additional two weeks.

The resulting transformed strain, *Streptomyces mobaraensis* BA13793 (pNGT207), was deposited with the Research Institute of Biotechnology and Industrial Technology, the Agency of Industrial Science and Technology (under the accession number of FERM P-14364). This strain was transferred on May 9, 1995 to international deposition based on the Budapest Treaty, and its accession number is FERM BP-5090.

Example 2
Procedure for the preparation of ED-110 by use of the transformed strain *Streptomyces lividans* TK21 (pNGT207)

*Streptomyces lividans* TK21 (pNGT207) strain which had been grown by slant culture on ISP2 medium containing 25 $\mu$g/ml of thiostrepton was inoculated into a 500 ml Erlenmeyer flask containing 110 ml of a culture medium (pH 7.2) composed of 2.0% glucose, 4% soluble starch, 0.3% yeast extract, 0.5% polypeptone, 1.0% corn gluten meal, 0.2% ammonium sulfate, 0.2% sodium chloride and 0.2% calcium carbonate, and incubated at 28° C. on a rotary shaker (180 revolutions per minute) for 2 days. Then, 1 ml each of this culture medium was inoculated into two 500 ml Erlenmeyer flasks containing 110 ml of a culture medium (pH 7.2) composed of 2.0% glucose, 6.0% soluble starch, 0.3% yeast extract, 0.5% polypeptone, 1.0% soya flour (manufactured by Nisshin Flour Milling Co., Ltd.), 0.2% sodium chloride, 0.2% ammonium sulfate, 0.2% calcium carbonate and 0.01% ferrous sulfate heptahydrate, and incubated under the same conditions as described above. After two days of incubation, 1 ml each of a methanol/tetrahydrofuran (1:1) mixture containing 120 mg of BE-13793C was added to the flasks, and the incubation was continued under the same conditions as described above for an additional 7 days.

The bacterial cells obtained by filtering the aforesaid culture media were extracted twice with 200 ml portions of tetrahydrofuran. After these extracts were combined and concentrated to dryness, 200 ml of water was added thereto. This mixture was extracted twice with 200 ml portions of ethyl acetate. After the resulting ethyl acetate layers were combined and concentrated to dryness, the resulting residue was subjected to column chromatography (2.0×40 cm) using silica gel (Kieselgel 60; manufactured by Merck), and developed with chloroform/methanol/tetrahydrofuran (4:1:1) to obtain fractions containing the desired compound. After these fractions were combined and concentrated to dryness, the resulting residue was dissolved in a small amount of methanol, subjected to column chromatography (1.5×60 cm) using Sephadex LH20 (manufactured by Pharmacia Co.), and eluted with methanol to obtain fractions containing the desired compound alone. These fractions were combined and concentrated to dryness to obtain 12.0 mg of the title compound.

Rf value: 0.51 [column, Kieselgel 60F$_{254}$ (manufactured by Merck); developing solvent, chloroform/methanol/tetrahydrofuran (2:1:1)].

HPLC: Rt 6.18 minutes [column, Chromatorex ODS having an inner diameter of 4.6 mm and a length of 250 mm; detection, UV 305 nm; flow rate, 1.0 ml/min.; mobile phase, methanol/water (3:1)].

FAB-MS (m/z): 519 [M]$^+$ $^1$H-NMR (400 MHz, DMSO-d$_6$, $\delta$ ppm): 11.0(1H, s), 10.9(1H, s), 10.3(1H, brs), 9.93(1H, brs), 8.69(1H, d, J=7.8 Hz), 8.51(1H, d, J=7.8 Hz), 7.17(2H, t, J=7.8 Hz), 7.05(1H, d, J=9.3 Hz), 7.01(1H, d, J=7.8 Hz), 6.99(1H, d, J=7.8 Hz), 5.41(1H, d, J=5.9 Hz), 5.34(1H, brs), 5.20(1H, d, J=5.4 Hz), 4.89(1H, brs), 4.02(2H, m), 3.74(1H, m), 3.63(2H, m), 3.41(1H, m).

Example 3
Procedure for the preparation of the compound of the formula

[IV]

by use of *Streptomyces lividans* TK-21 (pNGT207) strain

*Streptomyces lividans* TK21 (pNGT207) strain which had been grown on ISP2 slant agar medium containing 20 μg/ml of thiostrepton was inoculated into two 500 ml Erlenmeyer flasks containing 110 ml of a culture medium (pH 7.2 before sterilization) composed of 8.0% MS3600, 0.5% glucose, 0.25% L-threonine, 0.3% yeast extract, 0.1% magnesium sulfate hydrate, 0.2% calcium carbonate, 0.0002% ferrous sulfate, 0.00004% cupric chloride, 0.00004% manganese chloride, 0.00004% cobalt chloride, 0.0008% zinc sulfate, 0.00008% sodium borate, 0.00024% ammonium molybdate and 0.5% 3-(N-morpholino)propanesulfonic acid, and incubated at 28° C. on a rotary shaker (180 revolutions per minute) for 3 days. Then, 1 ml each of this culture medium was inoculated into one hundred 500 ml Erlenmeyer flasks containing 110 ml of a culture medium composed of the same components as described above, and incubated at 28° C. on a rotary shaker (180 revolutions per minute). After three days of incubation, 1 ml each of a methanol/tetrahydrofuran (3:1) mixture containing 10 mg of the compound of formula [VI] (Reference Example 1) was added to the flasks, and the incubation was continued under the same conditions as described above for an additional 11 days.

The bacterial cells obtained by filtering the aforesaid culture media were extracted twice with 5 L portions of methanol. After these extracts were combined and concentrated to remove the methanol, 1 L of water was added thereto. This mixture was successively extracted with 1.5 L, 1 L and 0.5 L of ethyl acetate. After the resulting ethyl acetate layers were combined and concentrated to dryness, the resulting residue was subjected to column chromatography (2.5×40 cm) using silica gel (Kieselgel 60; manufactured by Merck). The residue was washed with 1.5 L of chloroform/methanol (5:1) and eluted with a similar solvent system (3:1) to obtain fractions containing the desired compound. After these fractions were combined and concentrated to dryness, the resulting residue was dissolved in a small amount of ethanol, subjected to column chromatography (3×60 cm) using Sephadex LH20 (manufactured by Pharmacia Co.), and developed with ethanol to obtain fractions containing the desi red compound. These fractions were combined and concentrated to dryness to obtain 250 mg of the title compound.

Rf value: 0.19 [column, Kieselgel 60$F_{254}$ (manufactured by Merck); developing solvent, chloroform/methanol/tetrahydrofuran (3:1:1)].

HPLC: Rt 20.0 minutes (column, Chromatorex ODS having an inner diameter of 4.6 mm and a length of 250 mm; detection, UV 305 nm; flow rate, 1 ml/min.; mobile phase, a linear gradient from 50% to 100% methanol over a period of 30 minutes).

FAB-MS (m/z): 534 [M+H]$^+$ $^1$H-NMR (400 MHz, DMSO-d$_6$, δ ppm): 11.2(1H, s), 9.76(2H, brs), 8.88(1H, d, J=8.3 Hz), 8.80(1H, d, J=8.8 Hz), 7.18(1H, d, J=2.0 Hz), 6.98(1H, d, J=2.0 Hz), 6.83(1H, dd, J=8.3, 2.0 Hz), 6.80(1H, dd, J=8.8, 2.0 Hz), 5.98(1H, d, J=8.8 Hz), 5.87(1H, t, J=3.4 Hz), 5.35(1H, d, J=4.9 Hz), 5.13(1H, d, J=3.9 Hz), 4.95(1H, d, J=4.4 Hz), 4.01(1H, dd, J=10.7, 3.4 Hz), 3.91(2H, m), 3.77(1H, m), 5 3.51(2H, m), 3.15(3H, s).

Example 4

Procedure for the preparation of the compound of the formula

[V]

by use of *Streptomyces lividans* TK-21 (pNGT207) strain

*Streptomyces lividans* TK21 (pNGT207) strain which had been grown by slant culture on ISP2 medium containing 25 μg/ml of thiostrepton was inoculated into a 500 ml Erlenmeyer flask containing 110 ml of a culture medium (pH 7.2) composed of 2.0% glucose, 4% soluble starch, 0.3% yeast extract, 0.5% polypeptone, 1.0% corn gluten meal, 0.2% ammonium sulfate, 0.2% sodium chloride and 0.2% calcium carbonate, and incubated at 28° C. on a rotary shaker (180 revolutions per minute) for 2 days. Then, 1 ml each of this culture medium was inoculated into ten 500 ml Erlenmeyer flasks containing 110 ml of a culture medium (pH 7.2) composed of 2.0% glucose, 6.0% soluble starch, 0.3% yeast extract, 0.5% polypeptone, 1.0% soya flour (manufactured by Nisshin Flour Milling Co., Ltd.), 0.2% sodium chloride, 0.2% ammonium sulfate, 0.2% calcium carbonate and 0.01% ferrous sulfate heptahydrate, and incubated under the same conditions. After two days of incubation, 0.5 ml each of a dimethyl sulfoxide solution containing 10 mg of the compound of formula [VII] (Reference Example 2) was added to the flasks, and the incubation was continued under the same conditions as described above for an additional 7 days.

The bacterial cells obtained by filtering the aforesaid culture media were extracted with 500 ml of tetrahydrofuran. After this extract was concentrated to dryness, 200 ml of water was added thereto. This mixture was extracted twice with 200 ml portions of ethyl acetate. After the resulting ethyl acetate layers were combined and concentrated to dryness, the resulting residue was subjected to column chromatography (2.0×35 cm) using silica gel (Kieselgel 60; manufactured by Merck).

The residue was washed with 700 ml of chloroform/methanol/tetrahydrofuran/25% aqueous ammonia (20:10:10:1) and then 250 ml of a similar solvent system (20:40:10:1), and eluted with a similar solvent system (30:60:5:2) to obtain fractions containing the desired compound. After these fractions were combined and concentrated to dryness, the resulting residue was dissolved in a small amount of a methanol/tetrahydrofuran (1:1) mixture, subjected to column chromatography (1.5×25 cm) using Sephadex LH20 (manufactured by Pharmacia Co.), and developed with methanol/tetrahydrofuran (4:1). The resulting eluate was concentrated to dryness to obtain 17.6 mg of the title compound as a crude product. Moreover, 10 mg of this crude product was dissolved in 2.5 ml of tetrahydrofuran. After the addition of 5 ml of methanol, the resulting mixture was allowed to stand at 4° C. for 15 hours. Thus, 4.3 mg of the title compound was obtained.

Rf value: 0.28 [column, Kieselgel 60F$_{254}$ (manufactured by Merck); developing solvent, chloroform/methanol/tetrahydrofuran (3:1:1)].

HPLC: Rt 17.5 minutes (column, Chromatorex ODS having an inner diameter of 4.6 mm and a length of 250 mm; detection, UV 305 nm; flow rate, 1 ml/min.; mobile phase, a linear gradient from 50% to 100% methanol over a period of 30 minutes).

FAB-MS (m/z): 535 [M+H]$^+$ $^1$H-NMR (400 MHz, DMSO-d$_6$, δ ppm): 10.9(1H, s), 10.4(1H, s), 10.0(1H, s), 8.73(1H, d, J=7.8 Hz), 8.55(1H, d, J=7.8 Hz), 7.19(2H, t, J=7.8 Hz), 7.05(1H, d, J=9.3 Hz), 7.02(1H, d, J=7.8 Hz), 6.90(1H, d, J=7.8 Hz), 5.42(1H, d, J=5.9 Hz), 5.34(1H, brs), 5.22(1H, brs), 4.96(2H, brs), 4.91(1H, d, J=4.9 Hz), 4.01(2H, m), 3.74(1H, m), 3.63(2H, m), 3.39(1H, m).

Example 5

Procedure for the preparation of ED-110 by use of the transformed *Streptomyces mobaraensis* BA13793 (pNGT207) strain The transformed *Streptomyces mobaraensis* BA13793 (pNGT207) strain which had been grown by slant culture was inoculated into a 500 ml Erlenmeyer flask containing 110 ml of a culture medium (pH 7.2 before sterilization) composed of 0.1% glucose, 2.0% dextrin, 1.0% corn gluten meal, 0.5% fish meal, 0.1% yeast extract, 0.1% sodium chloride, 0.05% magnesium sulfate, 0.05% calcium chloride, 0.0002% ferrous sulfate, 0.00004% cupric chloride, 0.00004% manganese chloride, 0.00004% cobalt chloride, 0.00008% zinc sulfate, 0.00008% sodium borate, 0.00024% ammonium molybdate and 0.5% 3-(N-morpholino)propanesulfonic acid, and incubated at 28° C. on a rotary shaker (180 revolutions per minute) for 3 days.

Then, 2 ml each of this culture medium was inoculated into three 500 ml Erlenmeyer flasks containing 110 ml of a culture medium (pH 7.2 before sterilization) composed of 0.2% glucose, 4.0% dextrin, 1.5% corn gluten meal, 0.15% yeast extract, 3.0% fish meal, 0.1% sodium chloride, 0.05% magnesium sulfate, 0.05% calcium chloride, 0.0002% ferrous sulfate, 0.00004% cupric chloride, 0.00004% manganese chloride, 0.00004% cobalt chloride, 0.00008% zinc sulfate, 0.00008% sodium borate, 0.00024% ammonium molybdate and 0.5% 3-(N-morpholino)propanesulfonic acid, and incubated at 28° C. on a rotary shaker (180 revolutions per minute) for 17 days.

The bacterial cells obtained by filtering the aforesaid culture media were extracted twice with 500 ml portions of tetrahydrofuran. After these extracts were combined and concentrated to dryness, 300 ml of water was added thereto. This mixture was extracted twice with 300 ml portions of ethyl acetate. After the resulting ethyl acetate layers were combined and concentrated to dryness, the resulting residue was subjected to column chromatography (2.0×40 cm) using silica gel (Kieselgel 60; manufactured by Merck), and developed with chloroform/methanol/tetrahydrofuran (4:1:1) to obtain fractions containing the desired compound. After these fractions were combined and concentrated to dryness, the resulting residue was dissolved in a small amount of a methanol/tetrahydrofuran mixture and subjected to column chromatography (φ1.5×60 cm) using Sephadex LH20 (manufactured by Pharmacia Co.).

The residue was developed with methanol/tetrahydrofuran (5:1). After fractions containing the desired compound (ED-110) were combined and concentrated to dryness, the resulting residue was subjected to column chromatography (1.5×60 cm) using Sephadex LH20 (manufactured by Pharmacia Co.), and developed with ethanol. The resulting eluate was concentrated to dryness to obtain 68.3 mg of ED-110. In the aforesaid silica gel chromatography, 287.5 mg of BE-13793C was obtained by concentrating BE-13793C-containing fractions to dryness. The property data of ED-110 thus obtained were identical to those of ED-110 obtained in Example 2 by use of *Streptomyces lividans* TK-21 (pNGT207) strain.

Reference Example 1

Procedure for the preparation of the compound of the formula a) A tetrahydrofuran solution (0.93M, 6.9 ml) containing ethylmagnesium bromide was warmed to 45° C. and a toluene solution (7.8 ml) containing 6-methoxyindole (949 mg) was added thereto. After 40 minutes, a toluene solution (7.8 ml) containing 2,3-dibromo-N-methylmaleimide (388 mg) was added dropwise thereto over a period of 40 minutes, and the resulting mixture was refluxed for 2 hours. After the reaction mixture was cooled with ice, a 20% aqueous solution of citric acid was added thereto. This mixture was extracted with ethyl acetate, and the organic solvent layer was concentrated under reduced pressure. The resulting residue was subjected to Sephadex LH-20 column chromatography and developed with methanol to obtain 415 mg of 2,3-bis(6-methoxy-1H-indol-3-yl)-N-methylmaleimide (in a 72% yield).

b) 410 mg of the 2,3-bis(6-methoxy-1H-indol-3-yl)-N-methylmaleimide obtained in Reference Example 1-a), 255 mg of 2,3-dichloro-5,6-dicyano-1,4-benzoquinone (DDQ) and a catalytic amount of p-toluenesulfonic acid were added to 150 ml of dry benzene, and this mixture was refluxed in a stream of argon for 45 minutes. After the reaction mixture was cooled, a saturated aqueous solution of sodium thiosulfate was added thereto. This mixture was extracted with ethyl acetate. The organic layer was washed with a saturated aqueous solution of sodium hydrogen carbonate and then a saturated aqueous solution of sodium chloride, and concentrated under reduced pressure. The resulting residue as subjected to silica gel chromatography (chloroform/methanol/tetrahydrofuran=30:1:1) and developed with chloroform/methanol (10:1) to obtain 250 mg of trimethylarcyriaflavin C (in a 62% yield).

c) A mixture of 250 mg of the trimethylarcyriaflavin C obtained in Reference Example 1-b) and 2.2 g of pyridine hydrochloride was heated at 180° C. n a sealed tube for 90 minutes. The reaction mixture was cooled, diluted with N,N-dimethylformamide and 1N hydrochloric acid, and then extracted with ethyl acetate. The organic layer was washed with water and then a saturated aqueous solution of sodium chloride, and concentrated to dryness under reduced pressure. The resulting residue was subjected to Sephadex LH-20 column chromatography and developed with methanol to obtain 131 mg of the title compound of formula [VI] (6-methylarcyriaflavin C) (in a 56% yield).

FAB-MS (m/z): 372 [M+H]$^+$ $^1$H-NMR (300 MHz, DMSO-d$_6$, δ ppm): 11.35(2H, s), 9.73(2H, s), 8.70(2H, d, J=8.6 Hz), 7.04(2H, d, J=2.0 Hz), 6.78(2H, dd, J=8.6, 2.0 Hz), 3.14(3H, s).

Reference Example 2

Procedure for the preparation of the compound of the formula

[VII]

0.52 g of BE-13793C was dissolved in 3 ml of hydrazine hydrate (manufactured by Wako Pure Chemical Industries Ltd.), and this solution was stirred at room temperature for 1 hour. Then, concentrated hydrochloric acid was added thereto until the solution became acidic. The resulting precipitate was collected by filtration, washed with purified water, and dried under reduced pressure to obtain 0.53 g of the title compound of formula [VII] (in a 98% yield).

Rf value: 0.63 [column, Kieselgel 60F$_{254}$ (manufactured by Merck); developing solvent, chloroform/methanol/tetrahydrofuran (3:1:1)].

HPLC: 19.1 minutes (column, Chromatorex ODS having an inner diameter of 4.6 mm and a length of 250 mm; detection, UV 305 nm; flow rate, 1 ml/min.; mobile phase, a linear gradient from 50% to 100% methanol over a period of 30 minutes).

FAB-MS (m/z): 373 [M+H]$^+$ $^1$H-NMR (400 MHz, DMSO-d$_6$, δ ppm): 11.6(2H, s), 10.2(2H, s), 8.44(2H, d, J=7.8 Hz), 7.14(2H, t, J=7.8 Hz), 6.98(2H, d, J=7.8 Hz), 4.90(2H, s).

EXPLOITABILITY IN INDUSTRY

The present invention makes it possible to glycosylate indolopyrrolocarbazole derivatives conveniently and economically.

---

We claim:

1. Purified or isolated glycogyltransferase having the amino acid sequence represented by SEQ ID NO:1.

2. Isolated DNA encoding for the glycosyltransferase having the amino acid sequence as set forth in SEQ ID NO:1.

3. Isolated DNA having the base sequence represented by SEQ ID NO:2.

4. Isolated DNA encoding a glycosyltransferase which can convert a compound of the general formula (I)

wherein each of $X^1$ and $X^2$ is a hydrogen atom, a halogen atom, an amino group, a mono(lower alkyl)amino group, a di(lower alkyl)amino group, an aralkoxy group, a carboxyl group, a lower alkoxycarbonyl group, a lower alkanoyloxy group or a lower alkyl group; and R is a hydrogen atom, an amino groups a formylamino group, a lower alkanoylamino group, a mono(lower alkyl)amino. group, a di(lower alkyl) amino group, a hydroxyl group, a lower alkoxy group, an aralkoxy group, an aralkyl group or a lower alkyl group, to a compound of the general formula (II)

wherein $X^1$, $X^2$ and R have the same meanings as above, said DNA having the base sequence represented by SEQ ID NO:2.

5. Isolated DNA according to claim 4 having the same base pairs sequence as DNA from a microorganism belonging to the genus Saccharothrix.

6. Isolated DNA according to claim 5 wherein the microorganism belonging to the genus Saccharothrix is *Saccharothrix aerocolonigenes* ATCC39243 strain.

7. A recombinant plasmid DNA vector including the DNA according to any one of claims 4, 2 or 3.

8. A procaryotic host cell transformed with the recombinant vector according to claim 7 in a manner allowing the host cell to express said glycosyltransferase.

9. A transformed host cell obtained by transforming a bacterium producing a compound BE-13973C of the formula:

with a recombinant vector according to claim 7.

10. A transformed host cell obtained by transforming *Streptomyces mobaraensis* having the ability to produce the compound BE-13973C of the formula:

with a recombinant vector according to claim 7.

11. A process for the preparation of glycosyltransferase which comprises culturing a transformed host cell according to claim 8 to form and accumulate glycosyltransferase in the culture, and recovering glycosyltransferase from the culture.

12. A process for producing a compound of general formula (II)

wherein each of $X^1$ and $X^2$ is a hydrogen atom, a halogen atom, an amino group, a mono(lower alkyl)amino group, a di(lower alkyl)amino group, an aralkoxy group, a carboxyl group, a lower alkoxycarbonyl group, a lower alkanoyloxy group or a lower alkyl group; and R is a hydrogen atom, an amino group, a formylamino group, a lower alkanoylamino group, a mono(lower alkyl)amino group, a di(lower alkyl)amino group, a hydroxyl group, a lower alkoxy group, an aralkoxy group, an aralkyl group or a lower alkyl group, which comprises culturing a transformed host cell as set forth in claim 8 in the presence of an indolopyrrolocarbazole derivative of the general formula (I)

wherein $X^1$, $X^2$ and R have the same meanings as above, and recovering a compound of the general formula (II) from the resulting culture.

13. A process according to claim 12 wherein $X^1$ and $X^2$ are hydroxyl groups and R is a hydrogen atom, an amino group or a lower alkyl group.

14. A process for producing a compound of formula (III)

which comprises culturing a host cell as claimed in claim 9, and recovering the compound of the formula (III) from the resulting culture.

15. The process of claim 14 which comprises culturing a host cell which is a transformed host cell obtained by transforming *Streptomyces mobaraensis* having the ability to produce the compound BE-13973C with said recombinant vector.

* * * * *

SEQUENCE LISTING ( 1 ) GENERAL INFORMATION:

( i i i ) NUMBER OF SEQUENCES:2

( 2 ) INFORMATION FOR SEQ ID NO: 1:

( i ) SEQUENCE CHARACTERISTICS:
( A ) LENGTH:414 amino acids
( B ) TYPE:amino acids
( C ) TOPOLOGY:linear ( i i ) MOLECULE TYPE:protein ( x i ) SEQUENCE DESCRIPTION:SEQ ID NO:1:

```
Met Gly Ala Arg Val Leu Val Ala Thr Thr Pro Gly
 1               5                  10

Asp Gly His Val Asn Pro Met Val Pro Val Ala Gln
         15              20

Glu Met Val Ser Arg Gly His Glu Val Arg Trp Tyr
 25              30                  35

Thr Gly Lys Ala Phe Arg Ser Thr Val Glu Arg Thr
             40              45

Gly Ala Arg His Glu Pro Met Arg Asp Ala His Asp
     50              55                  60

Phe Gly Gly Met Pro Arg Glu Glu Ala Phe Pro Gln
                 65                  70

His Ala Gly Leu Thr Gly Ile Thr Gly Met Ile Ala
```

```
                         75                                    80
Gly  Phe  Arg  Asp  Ile  Phe  Ile  Glu  Pro  Ala  Ala  Asp
 85                      90                           95

Gln  Met  Thr  Asp  Leu  Leu  Ala  Leu  Leu  Glu  Asp  Phe
               100                 105

Pro  Ala  Asp  Val  Leu  Val  Thr  Asp  Glu  Thr  Phe  Phe
               110                 115                    120

Gly  Ala  Gly  Phe  Val  Ser  Glu  Arg  Thr  Gly  Ile  Pro
                    125                      130

Val  Ala  Trp  Ile  Ala  Thr  Ser  Ile  Tyr  Val  Phe  Ser
               135                 140

Ser  Arg  Asp  Thr  Ala  Pro  Leu  Gly  Leu  Gly  Leu  Pro
 145                     150                      155

Pro  Ser  Ser  Ser  Arg  Leu  Gly  Arg  Leu  Arg  Asn  Thr
               160                      165

Val  Leu  Lys  Gln  Leu  Thr  Asp  Arg  Val  Val  Met  Arg
 170                          175                          180

Asp  Leu  Arg  Arg  His  Ala  Asp  Val  Val  Arg  Asp  Arg
                    185                      190

Val  Gly  Leu  Pro  Arg  Ile  Arg  Lys  Gly  Ala  Phe  Glu
               195                      200

Asn  Ile  Met  Arg  Thr  Pro  Asp  Leu  Tyr  Leu  Leu  Gly
 205                          210                     215

Thr  Val  Pro  Ser  Phe  Glu  Tyr  Pro  Arg  Gly  Asp  Met
               220                           225

Pro  Pro  Glu  Val  Arg  Phe  Val  Gly  Pro  Phe  Val  Ser
      230                      235                          240

Pro  Ala  Pro  Pro  Asp  Phe  Thr  Pro  Pro  Ala  Trp  Trp
                    245                      250

Gly  Glu  Leu  Asp  Ser  Gly  Arg  Pro  Val  Val  His  Val
               255                 260

Thr  Gln  Gly  Thr  Val  Ala  Asn  Asp  Ala  Glu  Arg  Leu
 265                     270                      275

Leu  Leu  Pro  Ala  Ile  Arg  Ala  Leu  Ala  Ala  Glu  Asp
               280                      285

Val  Leu  Val  Val  Ala  Thr  Thr  Gly  Ala  Pro  Leu  Glu
      290                      295                          300

Leu  Glu  Pro  Met  Pro  Ala  Asn  Val  Arg  Val  Glu  Arg
                    305                           310

Phe  Ile  Pro  His  His  Ala  Leu  Leu  Pro  His  Val  Asp
               315                 320

Ala  Met  Val  Thr  Asn  Gly  Gly  Tyr  Gly  Gly  Val  Asn
 325                          330                     335

Thr  Ala  Leu  Ala  His  Gly  Val  Pro  Leu  Val  Val  Ala
               340                      345

Arg  Thr  Glu  Glu  Lys  His  Glu  Val  Ala  Ala  Arg  Val
      350                      355                          360

Ser  Trp  Ser  Gly  Ala  Gly  Val  His  Leu  Lys  Lys  Arg
                    365                      370

Arg  Leu  Ser  Glu  Arg  Asp  Ile  Arg  Arg  Ala  Val  Arg
               375                 380

Ala  Val  Leu  Asp  Glu  Pro  Arg  Phe  Arg  Val  His  Ala
 385                          390                     395
```

Ala Arg Leu Arg Asp Glu Tyr Ala Ala Arg Asp Ala
            400                     405

Val Val Asp Ala Ser Thr
    410

( 2 ) INFORMATION FOR SEQ ID NO: 2:

( i ) SEQUENCE CHARACTERISTICS:
        ( A ) LENGTH:1245 nucleotides
        ( B ) TYPE:nucleic acid
        ( C ) STRANDEDNESS:double- stranded
        ( D ) TOPOLOGY:linear     ( i i ) MOLECULE TYPE:Genomic DNA     ( v i ) ORIGINAL SOURCE:
        ( A ) ORGANISM:Saccharothrix aerocolonigenes     ( i x ) FEATURE:
        ( A ) NAME/KEY:ATCC39243

( x i ) SEQUENCE DESCRIPTION:SEQ ID NO:2:

| | | | |
|---|---|---|---|
| ATGGGGCAC | GAGTGCTGGT | GGCGACCACA | 30 |
| CCGGGGACG | GGCACGTCAA | CCCGATGGTG | 60 |
| CCGGTCGCCC | AGGAGATGGT | CAGCCGTGGA | 90 |
| CACGAGGTGC | GGTGGTACAC | GGGAAAGGCG | 120 |
| TTCCGCTCCA | CAGTGGAACG | AACAGGAGCC | 150 |
| CGCCACGAGC | CGATGCGCGA | CGCCCACGAC | 180 |
| TTCGGCGGCA | TGCCGAGGGA | GGAGGCGTTT | 210 |
| CCCCAGCACG | CGGGGCTGAC | CGGGATCACG | 240 |
| GGGATGATCG | CGGGGTTCAG | GGACATCTTC | 270 |
| ATCGAACCCG | CGGCCGACCA | GATGACAGAC | 300 |
| CTGCTGGCAC | TGCTGGAGGA | CTTCCCGGCC | 330 |
| GACGTGCTCG | TGACCGACGA | GACCTTCTTC | 360 |
| GGCGCGGGTT | TCGTCAGTGA | GCGCACGGGA | 390 |
| ATCCCCGTCG | CCTGGATCGC | CACGTCGATC | 420 |
| TACGTCTTCA | GCAGCCGCGA | CACGGCACCG | 450 |
| CTCGGGCTGG | GCCTGCCGCC | CAGCAGCTCC | 480 |
| AGGCTGGGCA | GGCTGCGCAA | CACCGTGCTC | 510 |
| AAACAGCTGA | CAGACCGTGT | CGTCATGCGA | 540 |
| GATCTCCGGC | GGCACGCGGA | CGTGGTGCGC | 570 |
| GACCGCGTCG | GCCTGCCCCG | CATCCGCAAG | 600 |
| GGGGCGTTCG | AGAACATCAT | GCGCACGCCC | 630 |
| GACCTCTACC | TGCTGGGCAC | CGTGCCGTCC | 660 |
| TTCGAGTACC | CGCGAGGCGA | CATGCCACCC | 690 |
| GAGGTGAGGT | TCGTCGGCCC | GTTCGTGAGC | 720 |
| CCTGCTCCGC | CGGACTTCAC | CCCACCGGCG | 750 |
| TGGTGGGGCG | AGCTCGACTC | CGGCCGGCCC | 780 |
| GTCGTCCACG | TCACCCAGGG | CACCGTCGCC | 810 |
| AACGACGCGG | AACGCCTGCT | GCTCCCCGCC | 840 |

| | | | |
|---|---|---|---|
| ATCCGAGCGC | TGGCAGCCGA | AGACGTGCTC | 870 |
| GTGGTCGCGA | CCACCGGTGC | CCCTCTGGAA | 900 |
| CTGGAGCCGA | TGCCGGCCAA | CGTGCGGGTG | 930 |
| GAACGGTTCA | TCCCGCATCA | CGCATTGCTT | 960 |
| CCCCACGTGG | ACGCCATGGT | GACCAACGGG | 990 |
| GGATACGGCG | GCGTCAACAC | GGCGCTCGCA | 1020 |
| CACGGCGTGC | CGCTGGTCGT | CGCGCGCACC | 1050 |
| GAGGAGAAGC | ACGAGGTCGC | GGCCAGAGTG | 1080 |
| AGCTGGTCAG | GTGCGGGTGT | TCACCTGAAG | 1110 |
| AAGCGCAGGC | TGTCCGAACG | GGACATCAGA | 1140 |
| CGGGCCGTGC | GCGCCGTTCT | CGACGAGCCG | 1170 |
| CGCTTCCGGG | TCCACGCGGC | GCGGCTGCGG | 1200 |
| GACGAGTACG | CGGCGCGCGA | CGCGGTCGTG | 1230 |
| GACGCGTCGA | CCTGA | | 1245 |